(12) United States Patent
Islam et al.

(10) Patent No.: US 6,495,017 B1
(45) Date of Patent: Dec. 17, 2002

(54) SAMPLE LOADING MEANS FOR ELECTROPHORESIS GEL STRIPS

(75) Inventors: Mohammed Rezaul Islam, Sunnyvale, CA (US); Robert S. Jetter, Oakland, CA (US)

(73) Assignee: Amersham Pharmacia Biotech, Inc., Piscataway, NJ (US)

( * ) Notice: Subject to any disclaimer, the term of this patent is extended or adjusted under 35 U.S.C. 154(b) by 0 days.

(21) Appl. No.: 09/546,360

(22) Filed: Apr. 10, 2000

(51) Int. Cl.[7] .............................................. G01N 27/453
(52) U.S. Cl. ...................... 204/616; 204/606
(58) Field of Search ................... 204/600, 606, 204/616, 618, 617

(56) References Cited

U.S. PATENT DOCUMENTS 6,113,766 A * 9/2000 Steiner et al. .............. 204/606

FOREIGN PATENT DOCUMENTS

| WO | WO 94/08234 | 4/1994 |
| WO | WO 98/57161 | 12/1998 |

* cited by examiner

*Primary Examiner*—Jill Warden
*Assistant Examiner*—Alex Noguerola
(74) *Attorney, Agent, or Firm*—Royal N. Ronning, Jr.; Stephen G. Ryan (57) ABSTRACT

An improved system for running electrophoresis gels "face up" is described. The system includes a single gel capacity strip holder, two electrodes, a sample cup, and a cover. The system provides a means of separating basic proteins on any length gel strip and the cup provides a user-friendly means of successfully putting the proteins on the gel face.

9 Claims, 7 Drawing Sheets

SAMPLE LOADING MEANS FOR ELECTROPHORESIS GEL STRIPS

FIELD OF THE INVENTION

The present invention relates to equipment and methods used in complex protein mixture analysis by 2-dimensional electrophoresis.

BACKGROUND OF THE INVENTION

For any type of detailed substance analysis, a homogeneous sample of the substance of interest is required. For this reason, isolating a substance of interest from a mixture of substances is often necessary in many biochemical laboratories. There are many ways to separate substances: on the basis of size by molecular sieve chromatography or SDS-PAGE, on the basis of binding properties by affinity chromatography, or by isoelectric points (the pH at which the substance has no net charge) by isoelectric focusing. Isoelectric focusing is particularly effective for analyzing microheterogeneous protein species or other species which differ slightly in their chemical. content.

Isoelectric focusing with an immobilized pH gradient (IPG), makes true isoelectric focusing possible and significantly improves the reproducibility of the spot distribution along the pH gradient axis of 2-D maps. IPG also makes it possible to focus basic proteins in the gel and to obtain Electrophoresis devices are well known in the art. However, attempts to construct an apparatus which successfully analyzes basic proteins (for example those with pH between 8–12) in a simple, user-friendly manner have previously been unsuccessful. Previous "face up" (gel side up) systems required messy preparation and critical setup to effectively load the sample on the gel. Sample cups had to be placed perfectly perpendicular to the gel (despite rotational freedom) and at the perfect height (despite placement flexibility on the vertical axis) using click stops to provide sample contact with the gel yet avoid crushing it. Newer "face down" (gel side down) systems which are easier to load and run, such as that described in co-assigned and application Ser. No. 09/095,002, now issued as U.S. Pat. No. 6,113,736, the contents of which are hereby incorporated by reference as if recited in full herein, cannot successfully separate basic proteins. Therefore, the present invention provides an apparatus which allows for effective analysis of basic proteins in a compact, simple way.

OBJECTS AND SUMMARY OF THE INVENTION

In view of the foregoing, it is an object of the present invention to provide a sample loading system that is capable of separating basic proteins by isoelectric focusing on an immobilized pH gradient (IPG) in a "face up" system.

It is also an object of the present invention to provide a sample loading means that is user-friendly and relatively clean.

It is another object of the present invention to simplify sample loading on "face up" gels.

It is a further object of the present invention to provide a means for accurate and uncomplicated sample positioning on the vertical axis, thereby providing adequate but not excessive contact of the sample and sample cup with the gel.

It is additionally an object of the present invention to create a gel loading system which is adjustable to different length gels and which allows flexibility of sample cup placement.

It is another object of the present invention to reduce the volume of mineral oil required to perform isoelectric focusing on a single gel.

These and other objects are satisfied by the present invention which is directed to gel loading systems, methods, and associated containers which are configured to successfully load electrophoresis gels with samples of any pH. In particular, a first aspect of the present invention is directed toward a sample loading assembly for electrophoresis gels comprising a gel holder adapted to hold a gel, two electrode carriers and associated electrodes, a sample loading cup adapted to load the sample onto the upper surface of the gel, and a cover, wherein said electrode carriers are configured such that, in ordinary use, the electrodes will be in electrical connection with the top surface of the gel. Specific embodiments include variations on the electrode placement along the gel surface and methods of electrode connection with the electrophoresis apparatus.

DETAILED DESCRIPTION OF THE PREFERRED EMBODIMENTS

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers and regions may be exaggerated for clarity.

Figure 1:
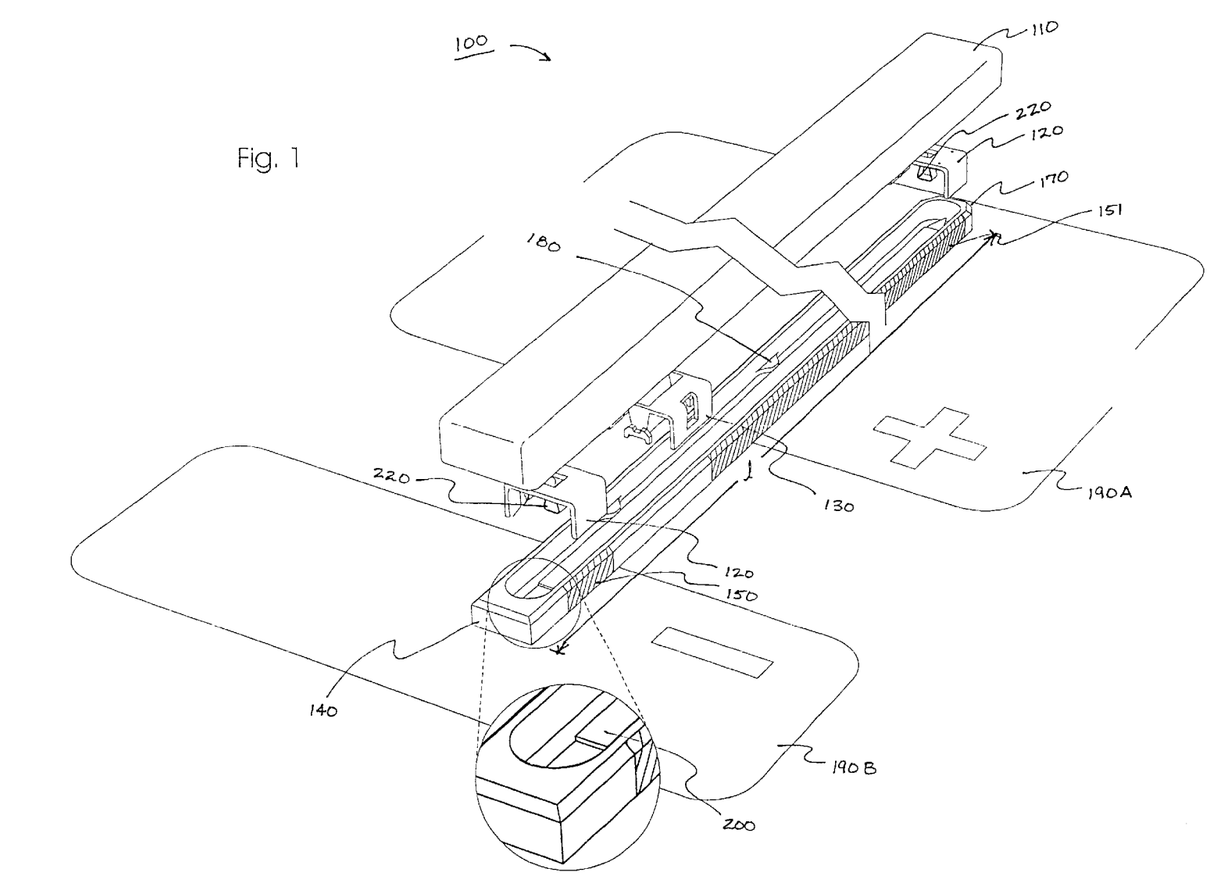
FIG. 1 is a perspective view of a strip holder, electrode, and sample loading cup according to the present invention.

Referring to the drawings, FIG. 1 illustrates a preferred sample loading assembly 100. As shown, the assembly 100 includes a gel strip holder 140, two electrode carriers 120, a sample loading cup 130, and a cover 110. The entire assembly 100 is preferably used in conjunction with an electrophoresis device such as the IPGphor Electrophoresis Unit (Hoefer Pharmacia Biotech Inc., San Francisco, Calif.). The electrophoresis device used in conjunction with the present invention preferably includes power transfer means such as power supply contact pads 190A, 190B.

Figure 1A:
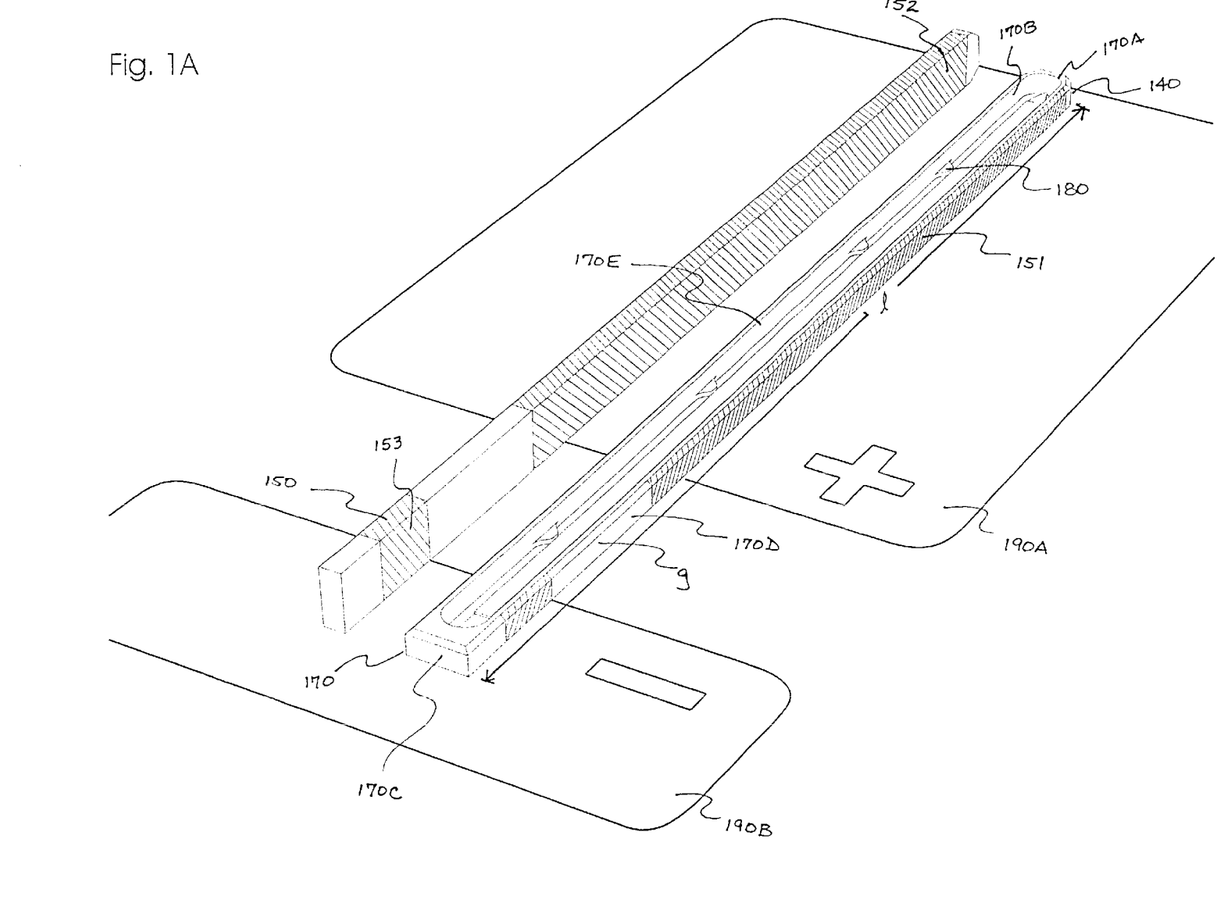
FIG. 1A is a bottom and side perspective view of the strip holder according to the present invention.

As shown in FIG. 1A, the gel strip holder 140 preferably comprises contiguous upstanding side walls 170A–170D arranged in a substantially rectangular shape to form a frame 170 with a longitudinal length "l". At one end of the frame 170, the walls 170A–170D are more preferably arranged to form a slight point which visibly distinguishes the end of the gel strip holder 140 which should contact an anodic power supply contact pad 190A from the more blunt end that should contact a cathodic power supply contact pad 190B. The frame 170 also has a bottom 170E which is contiguous to all the upstanding walls 170A–170D such that the walls 170A–170D and floor 170E of the frame 170 form a liquid-tight container.

In one preferred embodiment, the gel strip holder 140 preferably has electrode contact surface pairs 150, 151 on the longitudinal sides of the gel strip holder frame 170 (electrode contact surface 150, 151 is on both sides of the gel strip holder 140, only one side shown) as shown in FIG. 1A. There are preferably two electrode contact surface pairs 150, 151 with a non-conductive material between the pairs providing a gap "g" such that the the electrode contact surface pairs 150, 151 are not in electrical contact with each other. This enables the gel strip holder 140 to have one pair of electrically isolated (electrically isolated from the other pair) electrode contact surfaces 150, 151 for the anode and another for the cathode. Preferably, the gap "g" between the electrode contact surface pairs 150, 151. is no longer than the length of the gel. Additionally, a power contact surface 152, 153 on the bottom of the frame 170E electrically connects the pair of electrode contact surfaces 150, 151. The power contact surfaces 152, 153 thereby transfer power from the power supply contact pad 190A, 190B on the electrophoresis device to their corresponding pair of electrode contact surfaces 150, 151 when the gel strip holder 140 is placed on power supply contact pads 190A, 190B. Preferably, the power contact surfaces 152, 153 and electrode contact surfaces 150, 151 comprise an electrically conductive material which does not corrode or rust when exposed to mineral oil and/or water. Alternatively or additionally, a coating can provide corrosion resistance and/or electrical conductivity. A preferred coating for the electrode contact surfaces 150, 151 and power contact surfaces 152, 153 is two coats of moly manganese and one coat of nickel-plated oxide. In a preferred embodiment, as shown in FIG. 1A, the power contact surfaces 152, 153 extend at least partially lengthwise along the gel strip holder 140. As is known in the art, the power supply contact pads 190A, 190B can be constructed so that the contact pad for the cathode 190B is small to facilitate positioning of the gel strip holder 140 on the electrophoresis device. The power supply contact pad for the anode 190A, on the other hand, can advantageously be large to accommodate different length gels as described above. In one preferred embodiment, the power contact surfaces 152,153 are sufficiently short as to prevent shorting across the power supply contact pad 190A, 190B even if the gel strip holder 140 is placed on the power ,supply contact pad 190A, 190B backwards. Preferably, the power contact surface for the anode 152 and cathode 153 are sufficiently large to provide good electrical contact with the power supply contact pad 190A, 190B even when the power supply contact pad 190A, 190B is not perfectly flat.

Furthermore, the gel strip holder frame 170 preferably comprises a material that is nonconductive and provides efficient heat transfer and temperature control. One preferred material is aluminum oxide. The internal sides of the frame 170 are more preferably additionally chemically modified to minimize protein adsorption. Modifications of this type are well known to those of skill in the art, such as a gas phase silane treatment.

The holder 140 is furthermore preferably configured to hold a single gel strip 200 of any size, ranging in length from 7 cm to 24 cm. Advantageously, single gel capacity minimizes the volume of mineral oil required to fill the gel strip holder 140. As shown in FIGS. 1 and 1A, the gel strip holder 140 preferably additionally includes protrusions 180 on the inside of the frame 170, which contact a gel strip 200 when the gel 200 is in place and additionally keep the gel 200 substantially longitudinally straight. Preferably, these protrusions 180 are substantially small such that they do not inhibit movement of and contact with the sample loading cup 130 and electrode carriers 120 and associated electrodes 220 regardless of gel length as described hereinbelow. As shown in FIG. 1A, the protrusions 180 more preferably comprise substantially rounded geometries at the gel-protrusion interface, so as to not cut or damage the gel 200.

Figure 2:
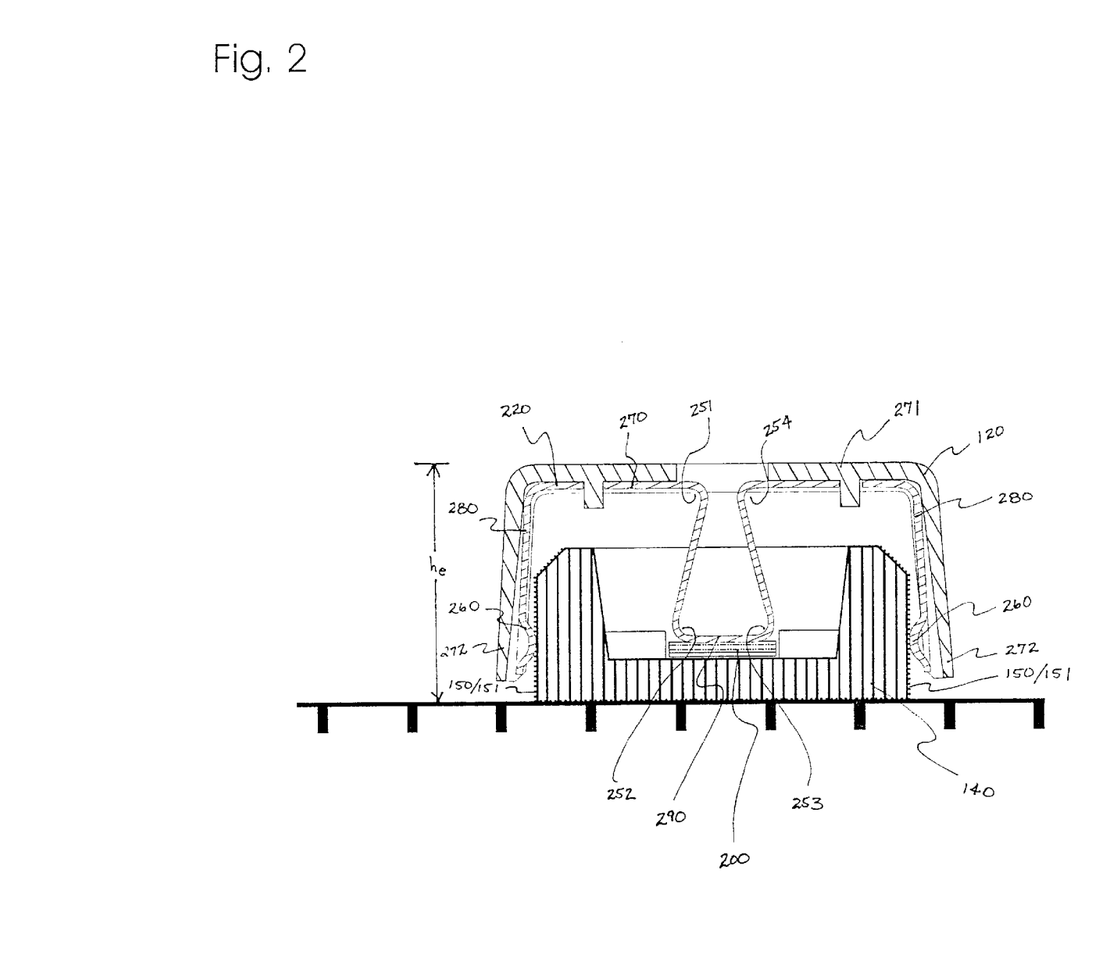
FIG. 2 is an enlarged view of the electrode and electrode carrier configuration according to the present invention.
Figure 2A:
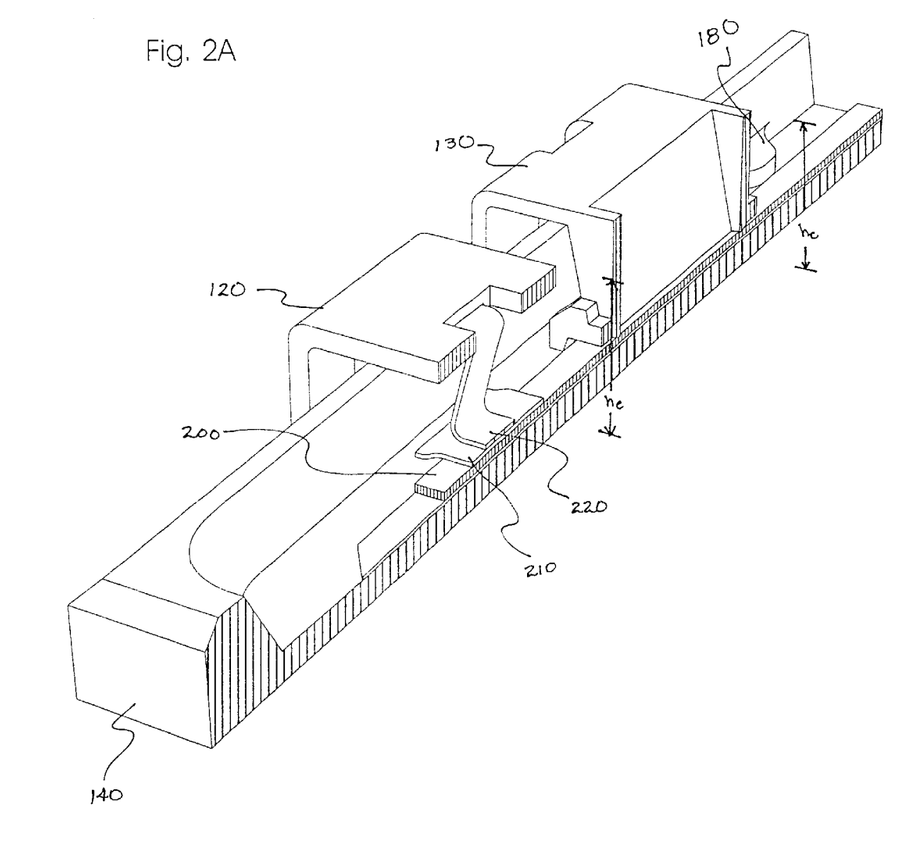
FIG. 2A is an enlarged cutaway perspective view of the electrode carrier and sample loading cup on a strip holder according to the present invention.

As shown in FIG. 2, in a preferred embodiment, the electrode carriers 120 preferably comprise two legs 272 and a body 271 connecting the two legs 272. The body 271 is preferably substantially perpendicular to the two legs 272 such that when the electrode carrier 120 is placed on top of the gel strip holder 140, the electrode carrier 120 wraps around the outside of the gel strip holder 140 as shown in FIG. 2. The electrode carriers 120 are preferably made of a nonconductive material such as polycarbonate.

Figure 2B:
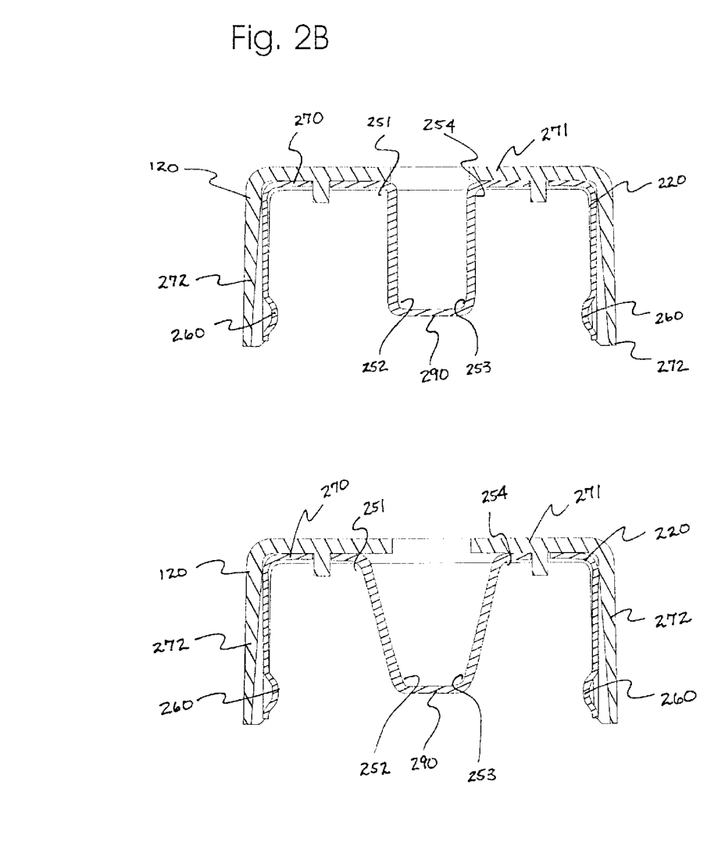
FIG. 2B is a cutoff side view of different electrode configurations on electrode carriers according to the present invention.
Figure 2C:
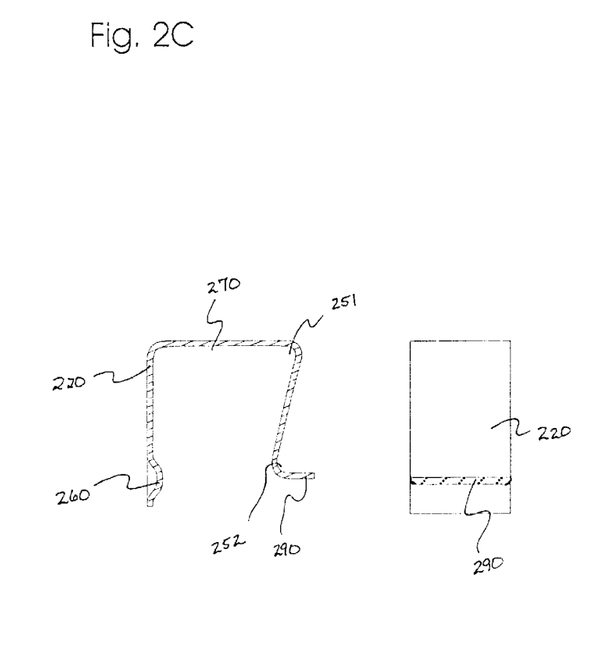
FIG. 2C is a cutoff front and cross sectional side view of half of an electrode, primarily illustrating the curved nature of the gel contact surface according to the present invention.

Each electrode carrier preferably is firmly attached to an electrode 220. More preferably, the electrodes 220 are comprised of two legs 280 and a body 270 which connects the two legs 280 at substantially right angles as shown in FIG. 2. Substantially near the center of the electrode body 270, the electrode 220 preferably projects substantially vertically downward at an angle 251. After a predetermined distance, the electrode preferably forms a second angle 252 to form a section which is substantially perpendicular to its legs 280. After a predetermined distance, the electrode 220 preferably projects upward again at a third angle 253 to the inner surface of the electrode carrier 120 and after a fourth angle 254, projects in substantially the same plane as the initial section of body 270. The lower section of electrode 220 that is perpendicular to the legs 280 forms a gel contact face 290. Preferably, all angles 251–254 are substantially the same magnitude so that the gel contact surface 290 is substantially parallel to the electrode body 270 as shown in FIG. 2. The projections therefore preferably form a loop which is substantially flat on the bottom as shown in FIG. 2. The electrode may be of many different shapes, as shown in FIG. 2B, as long as the gel contact surface 290 is flat. Preferably, the interior angles formed adjacent to the gel contact surface 290 (252, 253) are large enough to inhibit capillary wicking of any substance on or near the gel, and comprise substantially blunt edges to advantageously minimize the possibility of sharp corners damaging the gel as shown in FIG. 2C. The electrodes preferably comprise an electrically conductive material. More preferably, the electrodes comprise platinum-coated titanium.

In operation, the electrode carriers 120 are positioned on the gel strip holder 140 such that one electrode 220 is in electrical contact with the anode of the power supply contact pad 190A, and the other electrode 220 is in electrical contact with the cathode 190B of the power supply contact pad. To accommodate different length gels, the electrodes preferably can be placed at various longitudinal locations along the gel strip holder 140 while maintaining electrical contact with the power supply contact pads 190A, 190B as described above. Preferably, the electrodes 220 contact the power supply contact pads 190A, 190B via the electrode contact surfaces 150, 151 and the power contact surfaces 152, 153.

In a more preferred embodiment, the electrodes 220 also include at least one contact boss 260 to facilitate firm electrical contact with the electrode contact surfaces 150, 151 (FIG. 2). More preferably, the electrode 220 includes one contact boss 260 on each side. Additionally, the electrode carriers 120 and electrodes 220 are preferably sized and shaped such that the body of the electrode 270 and electrode carrier 271 act as springs which compress the two legs of the electrode 280 towards each other. This advantageously forces adequate electrical contact between the electrodes 220 and the electrode contact surfaces 150, 151.

Advantageously, the present invention allows for the addition of a filter paper wick 210 if necessary to absorb excess water and proteins beyond the pH range of the strip being used. Because the electrode holder 120 (and therefore the electrode 220) are not vertically physically supported by the gel strip holder 140 or power supply contact pads 190A, 190B, and because the electrode contact surface pairs 150, 151 preferably cover substantially the height of the gel strip holder 140, the electrode 220 within the electrode holder 120 advantageously has continuous height adjustment. Therefore, addition of filter paper wicks 210 of any reasonable height can be accommodated by the present invention. In a preferred embodiment, the force applied to the electrode holder 120 and electrode 220 from the cover 110 cause the electrode 220 to apply the optimal force to the gel strip 200 beneath it. Advantageously, in this embodiment, the electrodes 220 do not damage the gel 200 yet make sufficient contact with the gel 200 regardless of the presence or absence of a paper wick 210.

Figure 3:
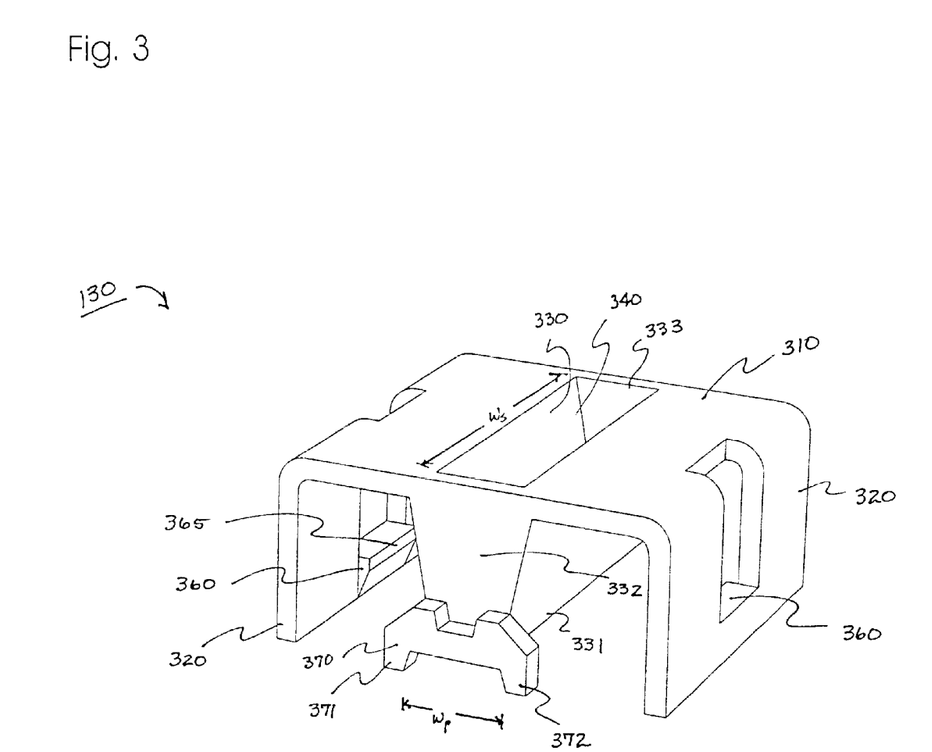
FIG. 3 is a perspective view of a sample loading cup according to the present invention.
Figure 3A:
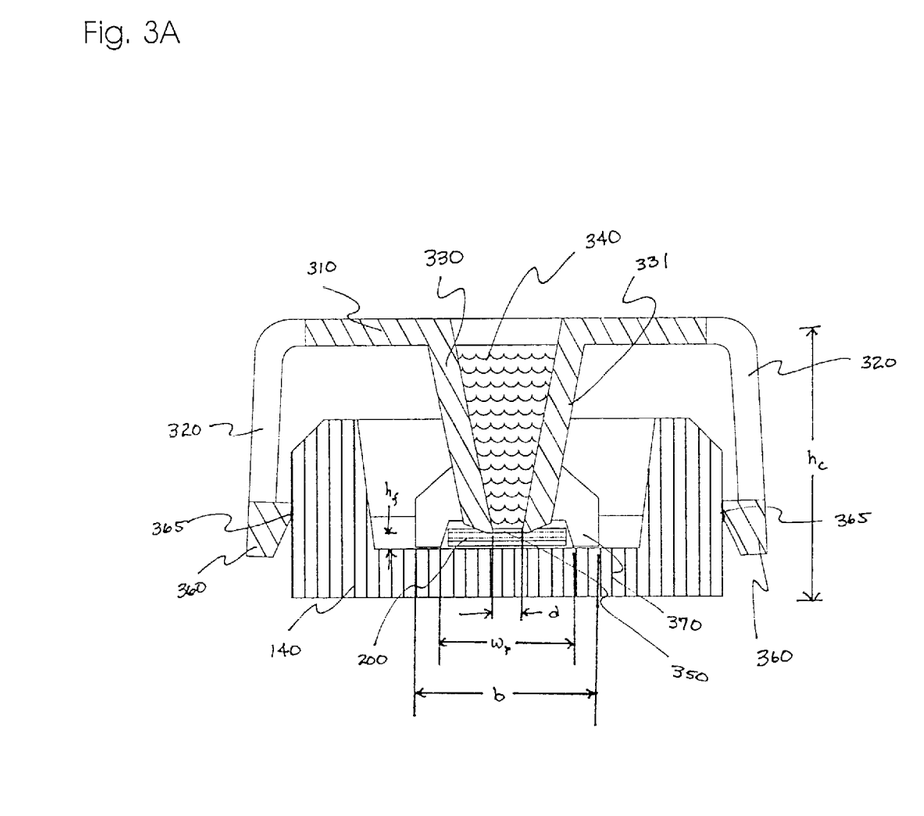
FIG. 3A is a cutoff front view of a sample loading cup on a strip holder according to the present invention.

To provide improved focusing patterns and give better resolution in conditions which entail substantial electroendosmosis, the present invention is designed to run electrophoresis "face up." Therefore, a means of loading sample from the top is required. A preferred embodiment of the sample loading cup 130 is shown in FIG. 3. The cup preferably comprises a non-conductive material such as a plastic or a ceramic to allow contact of the cup 130 with the electrode contact surfaces 150, 151 without deleterious effects. More preferably, the cup comprises a plastic such as polycarbonate. The sample loading cup 130 is preferably comprised of two legs 320 and a body 310 connecting them. Near approximately the center of the body 310, there are preferably two longitudinal slanted projections 330, 331 which project from the body 310 toward each other. Additionally, there are two substantially perpendicular projections 332, 333 which connect the two longitudinal slanted projections 330, 331 at their ends as shown in FIG. 3. These four projections 330–333 form an enclosure which acts as a sample chamber 340. Preferably, the projections 330–333 are sufficiently short and spaced apart such that they do not meet at the bottom as shown in FIG. 3A. Therefore, there is a slot 350 at the bottom of the sample chamber 340 which allows sample within the sample chamber 340 to contact the surface of the gel 200. Preferably, the slot 350 at the bottom is between 0.5 mm and 2 mm deep, and more preferably the slot is 0.9 mm deep (denoted "d" on FIG. 3A). Additionally, the sample chamber 130 is preferably the width (denoted "$w_s$" on FIG. 3) of the gel 200 or less to prevent leakage of sample into the gel strip holder 140 without contacting the gel 200.

More preferably, as shown in FIGS. 3 and 3A, the sample cup 130 further includes at least one friction block 360 on at least one leg 320. The friction block 360 preferably comprises a small flat sided projection which comprises a suitable contact surface 365 to contact the gel strip holder 140. The friction block 360 is preferably large enough to coerce contact between the gel strip holder 140 and the friction block 360 when the sample loading cup 130 is placed on the gel strip holder 140 as shown in FIG. 3A. The friction blocks 360 thereby advantageously keep the sample loading cup 130 at a specific longitudinal location relative to the gel strip holder 140. In a more preferred embodiment, the sample cup 130 can be placed almost anywhere along the gel strip holder 140 and held in place by at least one friction block 360.

Additionally, the sample loading cup 130 as shown in FIG. 3A also preferably comprises at least one standoff foot 370, and more preferably two or more. The standoff foot 370 includes two projections 371, 372 whose edges are spaced apart a distance "$w_p$" which is at least the width of a standard-sized rehydrated gel (approximately 3 mm). The standoff foot 370 therefore advantageously centers the gel 200 under the sample chamber 340. Additionally, the standoff foot 370 is preferably rigidly connected to the sample loading cup 130 and has a sufficiently wide base "b" to provide a stable mounting surface which prevents pivoting motions, thereby advantageously supplying good contact between the gel 200 and the sample loading cup 130 each time the cup 130 is put in place. Furthermore, the standoff foot 370 positions the sample loading cup 130 at the appropriate vertical height "$h_f$" so that the sample chamber 340 is suitably positioned in relationship to the gel 200 to contact but not crush the gel 200. This can be accomplished with a single standard size sample loading cup 130 with non-adjustable feet 370 because rehydrated gels 200 are substantially consistent in height (usually around 0.5 mm) regardless of length. A single-sized (i.e. non-adjustable) sample loading cup 130 is therefore advantageous because the operator does not need to adjust and align the sample loading cup 130 on the gel 200, thereby eliminating the possibility for human error.

In a more preferred embodiment, the standoff foot 370 is designed such that when the sample loading cup 130 and electrode carriers 120 are in place, the height "$h_c$" of the sample loading cup 130 is less than the height "$h_e$" (see FIG. 2) of the electrode carriers 120. Therefore, when a cover 110 is placed over the entire assembly as shown in FIG. 1, the cover 110 contacts only the body of the the electrode carriers 270 and not the body of the sample loading cup 310. This advantageously prevents any sample in the sample chamber 340 from exiting the chamber 340 through the top of the chamber 340 by capillary action.

The cover 110 preferably comprises a translucent or transparent non-conductive material. Preferably, the cover 110 is configured to fit loosely over the gel strip holder frame 170. Advantageously, the cover 110 additionally ensures electrical contact between the gel strip 200 and the electrodes 220 as discussed hereinabove. Furthermore, the cover 110 forces the electrodes 220 to retain their longitudinal location after placement. The use of a cover 110 additionally ensures that the power contact surfaces 152, 153 contact the power supply contact pads 190A, 190B because it applies pressure to the gel strip holder 140 power supply contact pads 190A, 190B interface when the cover of the electrophoresis machine (not shown) applies pressure to it.

In operation, the gel loading assembly 100 is assembled as follows. A gel 200 of the desired length is rehydrated face down in a separate container using mineral oil. The rehydrated gel 200 is then placed in the gel strip holder 140 such that the pointed side of the gel 200 is in the pointed side of the gel strip holder 140 and the blunt end of the gel 200 is at the blunt side of the gel strip holder 140. The gel strip holder 140 and gel 200 are then placed on an electrophoresis machine such that the power contact surfaces 152, 153 on the gel strip holder 140 contact the power supply contact pads 190A, 190B on the electrophoresis machine as shown in FIG. 1. An amount of mineral oil is then applied to the gel 200 in the gel strip holder 140 to submerge the gel 200 with mineral oil (generally between 2 to 10 mLs). At this point, the electrode carriers 120 are placed such that they straddle the gel strip holder 140 as shown in FIG. 2. The sample loading cup 130 is then similarly placed in the gel strip holder 140, making sure that the standoff feet 370 straddle the gel 200 and that the friction blocks 360 are in firm contact with the gel strip holder 140 as shown in FIG. 3. Finally, sample (up to 100 $\mu$L) is placed in the sample chamber 340 and the cover 110 is placed over the gel strip holder 140. If desired, a blotted wet paper wick 210 can be placed on the gel 200 (where the electrode 220 will be placed such that it ends up between the electrode 220 and the gel 200) before the electrode 220 is put in place.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A sample loading assembly for electrophoresis gels comprising a gel holder adapted to hold a gel having a top and a bottom surface, two electrode carriers adapted to be associated with electrodes, a sample loading cup, and a cover, wherein said electrode carriers are configured such that, the electrodes will be in electrical connection with the top surface of the gel and the electrode carriers are movable and can be placed at various longitudinal locations along the cover to accommodate different gel lengths.

2. The assembly of claim 1 wherein the electrode carriers are each attached to a separate electrode.

3. The assembly of claim 2 wherein the electrodes are arranged such that each electrode will be opposite the other and spaced apart sufficiently for electrophoresis to occur.

4. The assembly of claim 3 wherein the gel comprises an approximately rectangular strip and the electrodes are placed opposite each other at different longitudinal locations along the strip.

5. The assembly of claim 4 wherein the gel comprises a rectangular strip and the electrodes are placed at opposite ends of the strip.

6. The assembly of claim 2 wherein said electrodes are adapted to be in electrical contact with the anode and cathode of an electrophoresis apparatus.

7. The assembly of claim 6, wherein such electrical contact occurs in an anode and a cathode power supply contact pad.

8. The assembly of claim 7 wherein the electrodes further include at least one electrical contact boss to facilitate electrical contact with said power supply contact pad.

9. The assembly of claim 2 wherein said cup is in contact with said electrodes and further, wherein said cup is comprised of a non-conductive material.

\* \* \* \* \*